(12) United States Patent
Huang

(10) Patent No.: US 6,953,449 B2
(45) Date of Patent: Oct. 11, 2005

(54) HYPODERMIC SYRINGE HAVING PLUNGER PULL-OUT STOPPING STRUCTURE

(75) Inventor: Chin-Shu Huang, Hsinchu (TW)

(73) Assignee: Taiject Medical Device Co., Ltd., Hsin Chu Hsien (TW)

( * ) Notice: Subject to any disclaimer, the term of this patent is extended or adjusted under 35 U.S.C. 154(b) by 0 days.

(21) Appl. No.: 10/755,373

(22) Filed: Jan. 13, 2004

(65) Prior Publication Data

US 2004/0153037 A1 Aug. 5, 2004

(30) Foreign Application Priority Data

Jan. 17, 2003 (TW) ........................................ 92200861 U

(51) Int. Cl.⁷ ............................. A61M 5/00; A61M 5/32; A61M 5/315
(52) U.S. Cl. ......................... 604/225; 604/218; 604/110; 604/194
(58) Field of Search ......................... 604/110, 190–195, 604/220–225

(56) References Cited

U.S. PATENT DOCUMENTS 5,370,620 A * 12/1994 Shonfeld ................... 604/110
2003/0032928 A1 * 2/2003 Sudo et al. ................ 604/225

* cited by examiner

*Primary Examiner*—Nicholas D. Lucchesi
*Assistant Examiner*—Roz Maiorino
(74) *Attorney, Agent, or Firm*—Bacon & Thomas, PLLC

(57) ABSTRACT

A hypodermic syringe includes a barrel, the barrel having two stop portions in the rear side, a radially compressible constraint member mounted in the barrel and stopped between the stop portions of the barrel, and a plunger holding a rubber stopper and axially movably inserted through the constraint member into the inside of the barrel, the plunger having a breaking portion, and front stop flange, which is stopped against the constraint member upon back stroke of the plunger after use of the syringe for enabling the user to break the breaking portion.

11 Claims, 5 Drawing Sheets

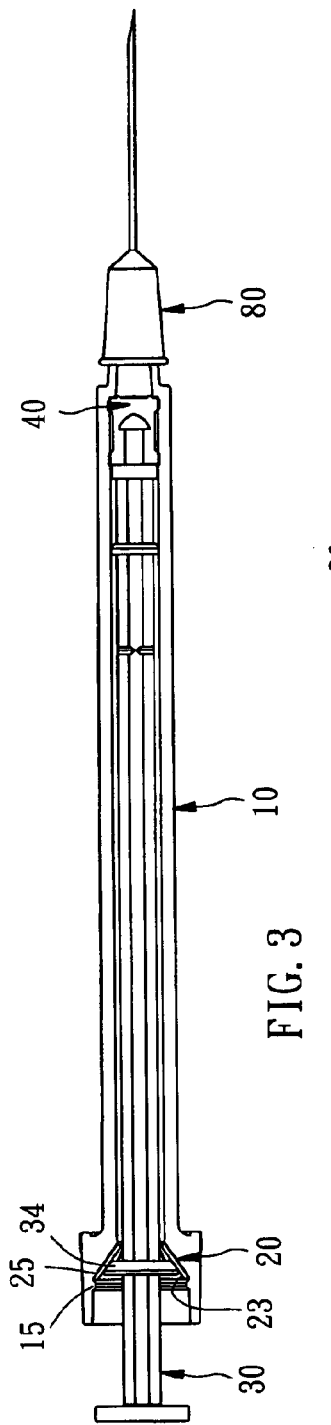
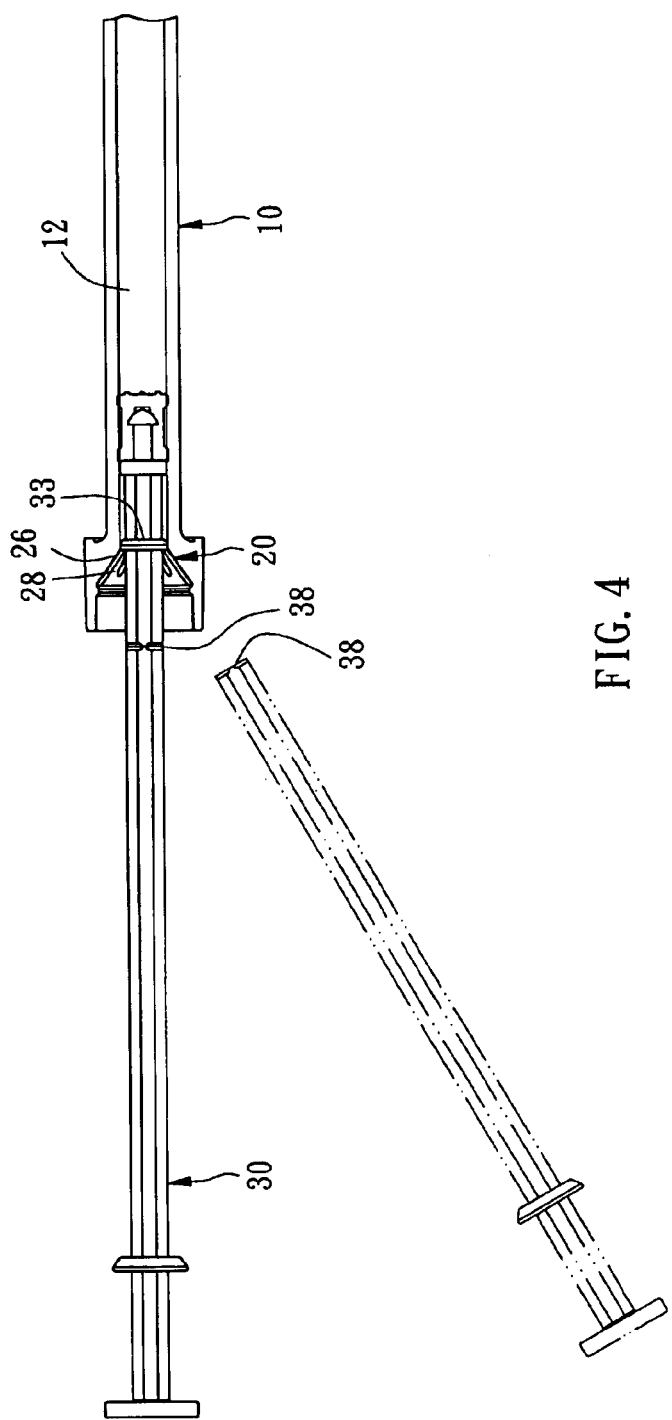
FIG. 3
FIG. 4

HYPODERMIC SYRINGE HAVING PLUNGER PULL-OUT STOPPING STRUCTURE

BACKGROUND OF THE INVENTION

1. Field of the Invention

The present invention relates generally to a hypodermic syringe and, more particularly, to such a hypodermic syringe having a plunger pull-out stopping structure.

2. Description of the Related Art

Regular hypodermic syringes are commonly designed having the plunger breakable after use of the syringe. A safety hypodermic syringe of this design has a stop flange formed on the inside wall of the barrel for stopping the plunger in position for breaking. However, this stop flange cannot positively stop the plunger inside the barrel. If the user pulled the plunger backwards from the barrel with an excessively high pulling force after use of the syringe, the plunger may be moved over the stop flange out of the barrel. If increasing the size of the stop flange is increased to prevent the plunger from falling out of the barrel, the installation of the plunger in the barrel becomes difficult.

SUMMARY OF THE INVENTION

The present invention has been accomplished under the circumstances in view. It is the main object of the present invention to provide a hypodermic syringe, which uses a constraint member in the rear end of the barrel to facilitate installation of the plunger. It is another object of the present invention to provide a hypodermic syringe, which uses a constraint member in the rear end of the barrel to stop the plunger positively in position for breaking after use of the syringe.

To achieve these and other objects of the present invention, the hypodermic syringe comprises a barrel, the barrel having a hollow cylindrical body defining a longitudinally extended through hole, a first stop portion and a second stop portion formed in the longitudinally extended through hole near a rear end of the body of the barrel, and a receiving chamber defined between the first stop portion and the second stop portion; a constraint member shaped like a hollow conical cap having a relatively greater rear side and a relatively smaller front side and mounted in the receiving chamber inside the barrel, the constraint member having an outer stop face stopped against the first stop portion of the barrel, and inner stop face, a rear stop edge formed on the relatively greater rear side of the constraint member and stopped against the second stop portion of the barrel, a front stop edge formed on the relatively smaller front side of the constraint member, and a radial crevice; and a plunger, the plunger having an elongated stem inserted through the constraint member into the inside of the through hole of the barrel, a front stop flange extended around the periphery of the stem near a front end of the stem and movable with the plunger in the through hole of the barrel and to be stopped at the front stop edge of the constraint member upon a back stroke of the plunger relative to the barrel, and a thumb rest formed on a rear end of the stem.

BRIEF DESCRIPTION OF THE DRAWINGS

FIG. 3 is a sectional assembly view of the hypodermic syringe according to the present invention.

FIG. 4 is schematic drawing similar to FIG. 3 but showing the plunger pulled to the rear side of the barrel and set in position.

DETAILED DESCRIPTION OF THE INVENTION

Figure 1:
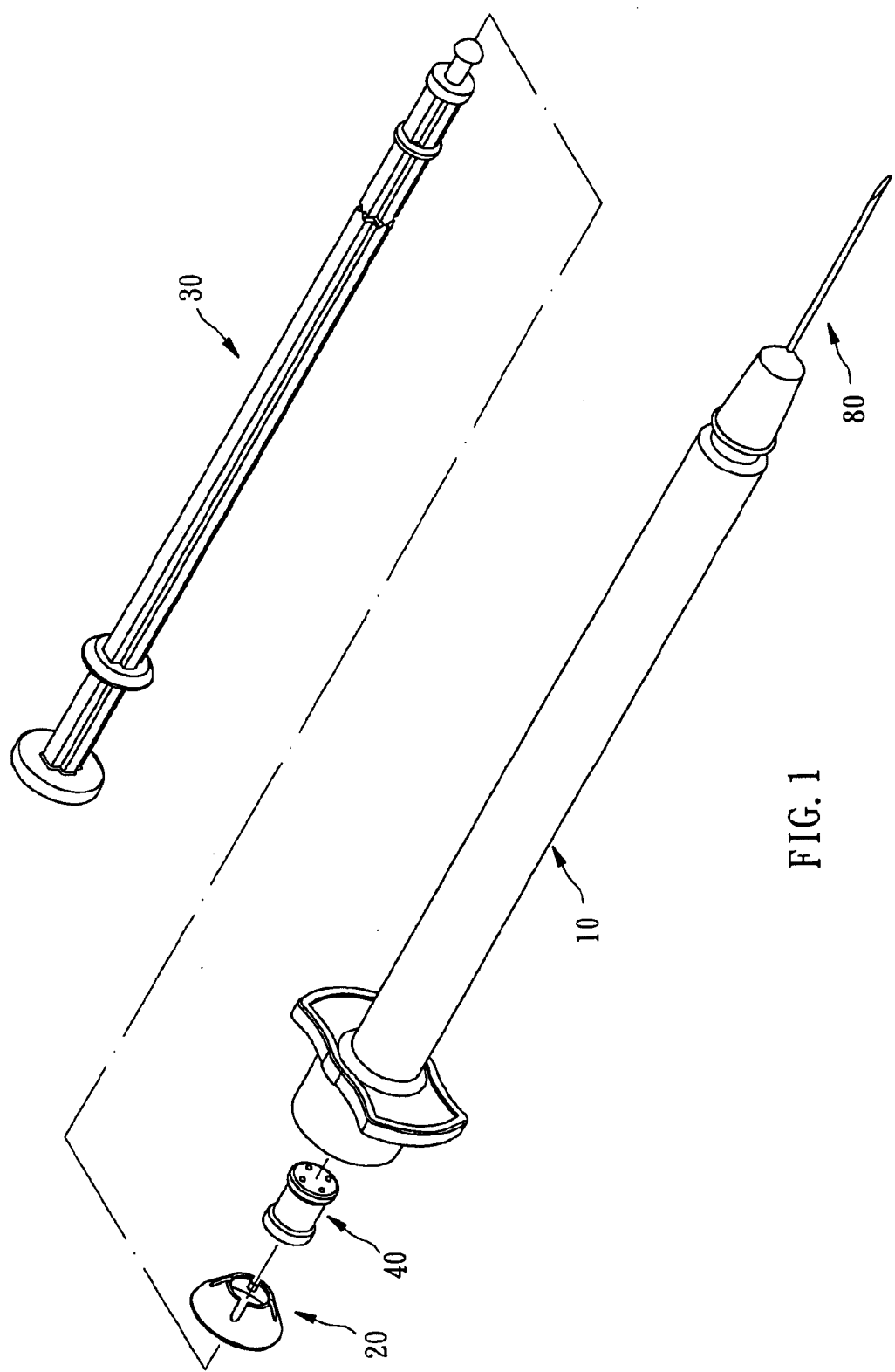
FIG. 1 is an exploded view of a hypodermic syringe according to the present invention.
Figure 2:
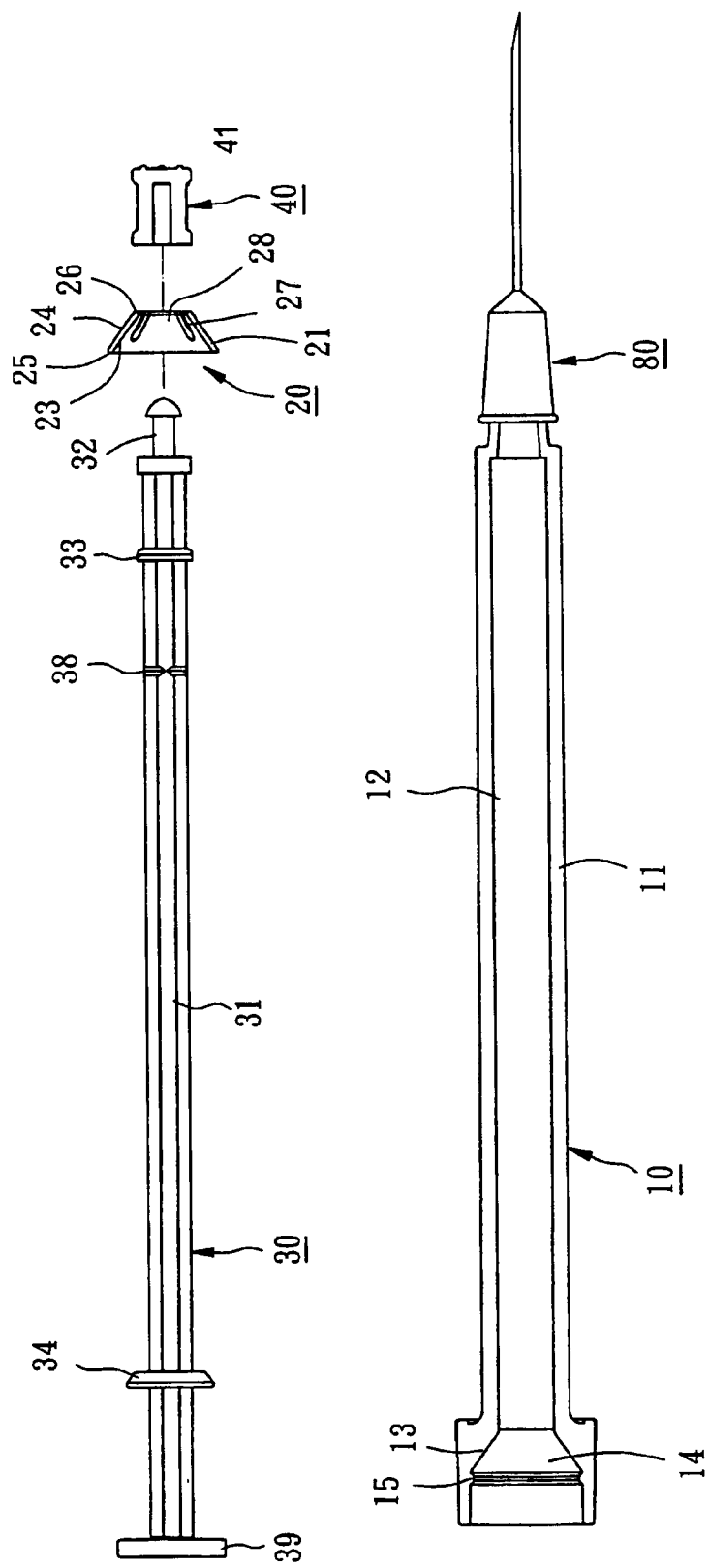
FIG. 2 is an exploded side plain view of the hypodermic syringe according to the present invention.

Referring to FIGS. 1~4, a hypodermic syringe is shown to be used with a needle cannula 80. The hypodermic syringe is comprised of a barrel 10, a constraint member 20, a plunger 30, and a rubber stopper 40.

The barrel 10 has a hollow cylindrical body 11 defining a longitudinally extended through hole 12, a first stop portion 13 formed in the longitudinally extended through hole 12 near the rear end and shaped like a taper hole having a diameter gradually increasing toward the rear end of the longitudinally extended through hole 12, a receiving chamber 14 defined within the first stop portion 13, and a second stop portion 15 formed in the longitudinally extended through hole 12 around the rear side of the receiving chamber 14. The second stop portion 15 according to the present preferred embodiment is a stop flange.

The constraint member 20 is shaped like a hollow conical cap having an inner stop face 23 and an outer stop face 24 on the inner and outer side of the body 21 thereof, a rear stop edge 25 and a front stop edge 26 respectively formed on the relatively greater bottom side and the relatively smaller front side, four radial crevices 27 equiangularly spaced around the periphery and radially extended from the front stop edge 26, and four retaining spring strips 28 formed of portions of the body 21 and equiangularly spaced around the periphery of the body 21 and respectively separated from one another by the radial crevices 27. The outer stop face 24 is to be stopped against the first stop portion 13 of the barrel 10. The rear stop edge 25 is to be stopped against the second stop portion 15 of the barrel 10.

The plunger 30 has an elongated stem 31, a retaining rod 32 axially forwardly extended from the front end of the stem 31, a front stop flange 33 extended around the periphery of the stem 31 near the retaining rod 32, a rear stop flange 34 extended around the periphery of the stem 31 near the rear end, a breaking portion 38 formed in the stem 31 at a suitable location for enabling the stem 31 to be conveniently broken after use of the hypodermic syringe, and a thumb rest 39 formed on the rear end of the stem 31.

The rubber stopper 40 is fastened to the retaining rod 32 of the plunger 30, having a stopper body 41 movable with the plunger 30 in the through hole 12 of the barrel 10 and peripherally disposed in close contact with the inside wall of the barrel 10.

The operation of the hypodermic syringe is outlined hereinafter. During installation, the body 21 of the constraint member 20 is stopped between the first stop portion 13 and second stop portion 14 of the barrel 10, and prohibited from axial movement.

Thereafter, the stem 31 of the plunger 30 is inserted through the constraint member 20 to force the retaining spring strips 28 radially outwards, for enabling the rubber stopper 40 and the front stop flange 33 to be moved through the constraint member 20 into the inside of the through hole 12 of the barrel 10.

As illustrated in FIG. 3, when pushing the plunger 30 to the end, the rear stop flange 34 is stopped at the body 21 of the constraint member 20. Therefore, the rear stop flange 34 can be moved with the plunger 30 to move the constraint member 20 to the position in between the first stop portion 13 and second stop portion 15 of the barrel 10.

FIG. 4 shows the plunger 30 pulled back after use of the hypodermic syringe. As illustrated, the front stop flange 33 is stopped against the retaining spring strips 28 of the constraint member 20, prohibiting further backward movement of the plunger 30 relative to the barrel 10. At this time, the user can bend the plunger 30 to break the breaking portion 38, preventing a reuse of the hypodermic syringe.

Figure 7:
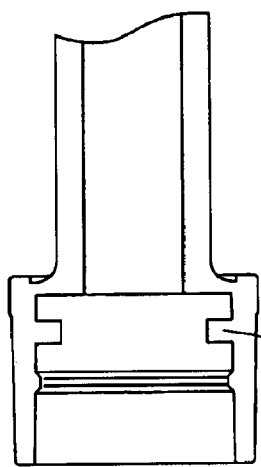
FIG. 7 is a schematic drawing showing still another alternate form of the barrel for the hypodermic syringe according to the present invention.
Figure 5:
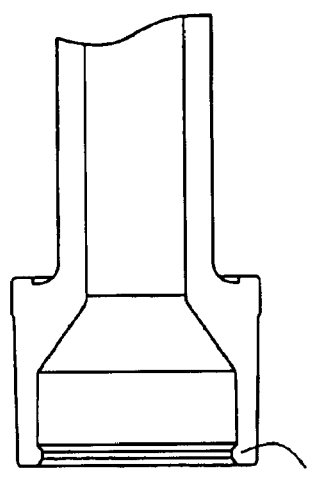
FIG. 5 is a schematic drawing showing an alternate form of the barrel for the hypodermic syringe according to the present invention.
Figure 6:
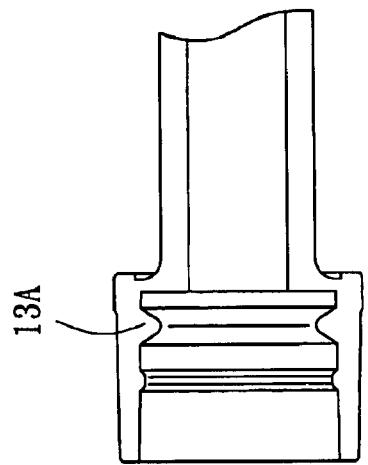
FIG. 6 is a schematic drawing showing another alternate form of the barrel for the hypodermic syringe according to the present invention.

The first and second stop portions of the barrel 10 may be variously embodied. AS shown in FIG. 5, the second stop portion 15A of the barrel can be formed in the rear end (rear orifice) of the barrel. As shown in FIG. 6, the first stop portion 13A can be an inside annular flange having a triangular cross section. As shown in FIG. 7, the first stop portion 13B can be an inside annular flange having a rectangular cross section.

Figure 8:
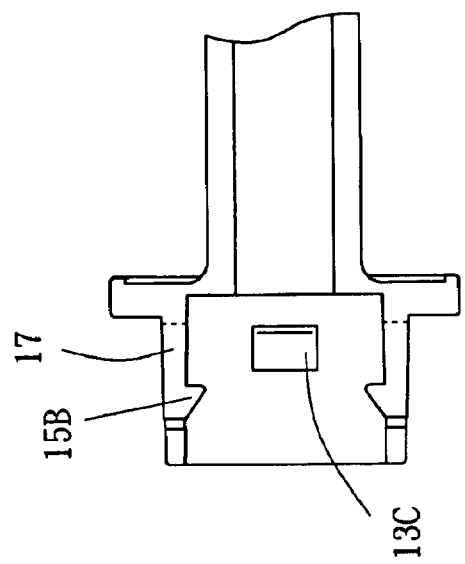
FIG. 8 is a schematic drawing showing still another alternate form of the barrel for the hypodermic syringe according to the present invention.
Figure 9:
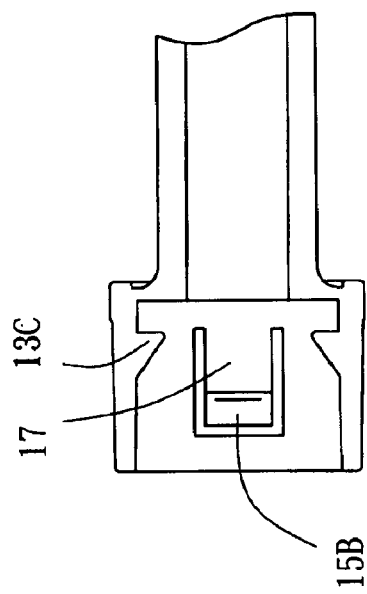
FIG. 9 is a side view of FIG. 8.

In order to facilitate the installation of the constraint member 20 in the barrel 10, the barrel 10 may be made as follows:

As shown in FIGS. 8 and 9, the constraint member is formed integral with the barrel, having backwardly extended two spring strips 17, two first stop portions 13c protruded from the inside wall of the barrel, and two second stop portions 15B respectively formed on the free end of each spring strip 17.

Figure 10:
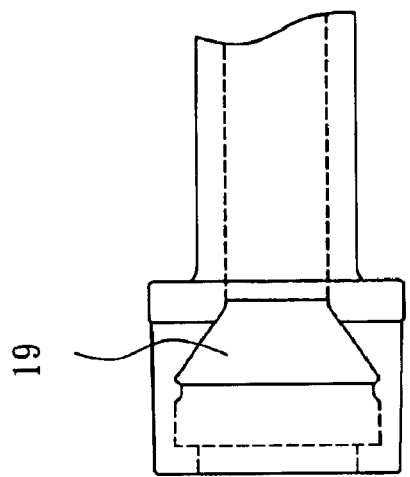
FIG. 10 is a schematic drawing showing still another alternate form of the barrel for the hypodermic syringe according to the present invention.

Referring to FIG. 10, the barrel can be made having a radially extended mounting hole 19 for the installation of the constraint member 20 from the lateral side. This design makes the installation of the constraint member 20 easy.

Figure 11:
FIG. 11 is an elevational view of an alternate form of the constraint member for the hypodermic syringe according to the present invention.

Referring to FIG. 11, the constraint member can be made having additional radial crevices 29 extended to the relatively greater rear side so that the rear side of the constraint member is deformable for easy installation in the second stop portion of the barrel.

Figure 12:
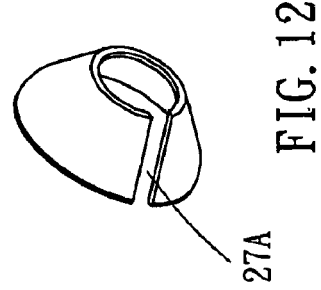
FIG. 12 is an elevational view of another alternate form of the constraint member for the hypodermic syringe according to the present invention.

Referring to FIG. 12, the constraint member can be made in the shape of a tapered ring having a crevice 27A cut through the front and rear sides. According to this design, the constraint member is radially compressible.

As indicated above, the invention has the following features:

1. The design of the stop flanges of the plunger enables the plunger to be conveniently installed in the through hole of the barrel.

2. The design of the stop flanges of the plunger enables the plunger to be positively stopped in the rear side of the barrel for breaking after use of the hypodermic syringe.

What is claimed is:

1. A hypodermic syringe comprising:
   a barrel, said barrel having a hollow cylindrical body defining a longitudinally extended through hole, a first stop portion and a second stop portion formed in said longitudinally extended through hole near a rear end of said body of said barrel, and a receiving chamber defined between said first stop portion and said second stop portion;
   a constraint member shaped like a hollow conical cap having relatively greater rear side and a relatively smaller front side and mounted in said receiving chamber inside said barrel, said constraint member having an outer stop face stopped against said first stop portion of said barrel, and an inner stop face, a rear stop edge formed on the relatively greater rear side of said constraint member and stopped against said second stop portion of said barrel, a front stop edge formed on the relatively smaller front side of said constraint member, and at least one radial crevice; and
   a plunger, said plunger having an elongated stem inserted through said constraint member into the inside of said through hole of said barrel, a front stop flange extended around the periphery of said stem near a front end of said stem and movable with said plunger into said through hole of said barrel and to be stopped at said front stop edge of said constraint member upon a back stroke of said plunger relative to said barrel, and a thumb rest formed on a rear end of said stem.

2. The hypodermic syringe as claimed in claim 1, wherein said first stop portion of said barrel has a triangular cross section.

3. The hypodermic syringe as claimed in claim 1, wherein said first stop portion of said barrel is an annular flange formed integral with an inside wall of said barrel.

4. The hypodermic syringe as claimed in claim 1, wherein said barrel has a spring strip, said spring strip having a free end forming said first stop portion of said barrel.

5. The hypodermic syringe as claimed in claim 1, wherein said barrel has a mounting hole in the periphery of hollow cylindrical body thereof through which said constraint member is inserted into the inside of said receiving chamber.

6. The hypodermic syringe as claimed in claim 1, wherein the number of the radial crevice of said constraint member is four, and said four radial crevices separating the peripheral wall of said constraint member to form four retaining spring strips.

7. The hypodermic syringe as claimed in claim 1, wherein the number of the radial crevice of said constraint member is one, and said radial crevice extends through the front and rear sides of said constraint member.

8. The hypodermic syringe as claimed in claim 1, wherein said constraint member further has a second radial crevice extended from said rear stop edge.

9. The hypodermic syringe as claimed in claim 1, further comprising a rubber stopper fastened to the front end of said stern.

10. The hypodermic syringe as claimed in claim 1, wherein said first stop portion of said barrel is shaped like a taper hole having diameter gradually increasing toward said second stop portion of said barrel.

11. The hypodermic syringe of claim 1, wherein said plunger includes a breaking portion formed in the stem at a predetermined location to break the stem after use of the syringe upon the stoppage of the front stop flange at the front stop edge of the constraint member when pulling back said plunger.

* * * * *